United States Patent [19]

Boone

[11] Patent Number: 5,107,529
[45] Date of Patent: Apr. 21, 1992

[54] RADIOGRAPHIC EQUALIZATION APPARATUS AND METHOD

[75] Inventor: John M. Boone, Radnor, Pa.

[73] Assignee: Thomas Jefferson University, Philadelphia, Pa.

[21] Appl. No.: 592,137

[22] Filed: Oct. 3, 1990

[51] Int. Cl.$^5$ .............................................. G21K 1/00
[52] U.S. Cl. .................................... 378/157; 378/156; 378/158; 359/890
[58] Field of Search ............... 378/156, 157, 158, 159; 350/313, 311, 315, 316

[56] References Cited

U.S. PATENT DOCUMENTS

| | | | |
|---|---|---|---|
| 3,248,547 | 4/1986 | Van De Geijn | 250/86 |
| 4,286,167 | 4/1981 | LaRiviere | 250/510 |
| 4,392,239 | 7/1983 | Wilkens | 378/146 |
| 4,400,827 | 8/1983 | Spears | 378/159 |
| 4,481,419 | 11/1984 | Persyk | 578/159 |
| 4,675,893 | 6/1987 | Duinker et al. | 378/151 |
| 4,677,652 | 6/1987 | Duinker et al. | 378/151 |
| 4,727,561 | 2/1988 | Fujisaki | 378/158 |
| 4,741,012 | 4/1988 | Duinker et al. | 378/145 |
| 4,800,474 | 1/1989 | Bornhorst | 350/315 |
| 4,868,857 | 9/1989 | Dobbins, III | 378/159 |
| 4,890,312 | 12/1989 | Duinker | 378/146 |

FOREIGN PATENT DOCUMENTS

WO89/02645 3/1989 PCT Int'l Appl.
0682860 8/1979 U.S.S.R. ............................. 350/316

OTHER PUBLICATIONS

"A Scanning System for Chest Radiography with Regional Exposure Control: Practical Implementation", Plewes, D. B. et al., *Medical Physics,* vol. 10, No. 5, Sep./Oct. 1983.

"A Scanning System for Chest Radiography with Regional Exposure Control: Theoretical Considerations", Plewes, D. B., *Medical Physics,* vol. 10, No. 5, Sep./Oct. 1983.

"AMBER: A Scanning Multiple-Beam Equalization System for Chest Radiography", Vlasbloem, Hugo et al., *Radiology,* vol. 169, No. 1, pp. 29-34.

"Digital Beam Attenuator Technique for Compensated Chest Radiography", Hasegawa, Bruce H. et al., *Radiology,* vol. 159, No. 2, pp. 537-543.

"Adaptive Histogram Equalization and Its Variations", Pizer, Stephen M. et al., *Computer Vision, Graphics and Image Processing* 39, 1987, pp. 355-368.

"Space 107—Light Equalization Radiography", Kruger, Robert A. et al., *Scientific Exhibits—CHEST,* vol. 173(P).

"No. 1105—Spectroscopic Imaging with Color Display", Boone, John M. et al., *Works in Progress—PHYSICS/Radiology,* 1987.

*Primary Examiner*—Janice A. Howell
*Assistant Examiner*—David P. Porta
*Attorney, Agent, or Firm*—Woodcock Washburn Kurtz Mackiewicz & Norris

[57] ABSTRACT

A radiographic equalization apparatus comprises a plurality of juxtaposed disks each having a plurality of unique filtration patterns annularly disposed therearound. The disks are rotated relative to one another to obtain a unique attenuation pattern for correcting for overexposures in an x-ray image.

29 Claims, 3 Drawing Sheets

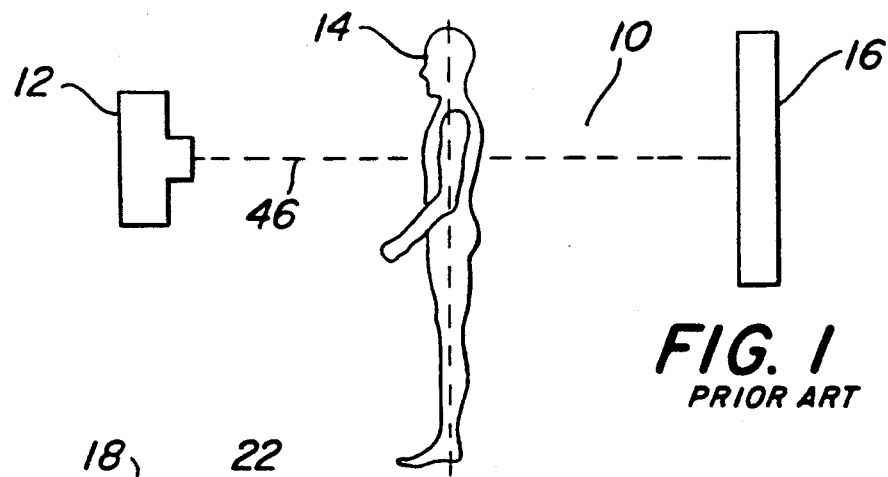
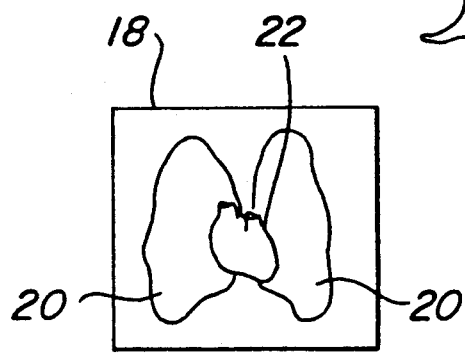
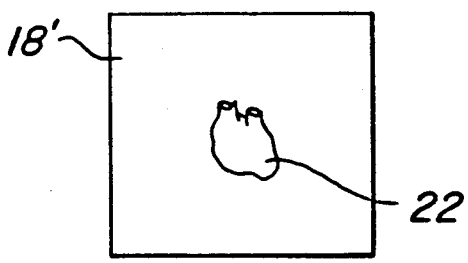
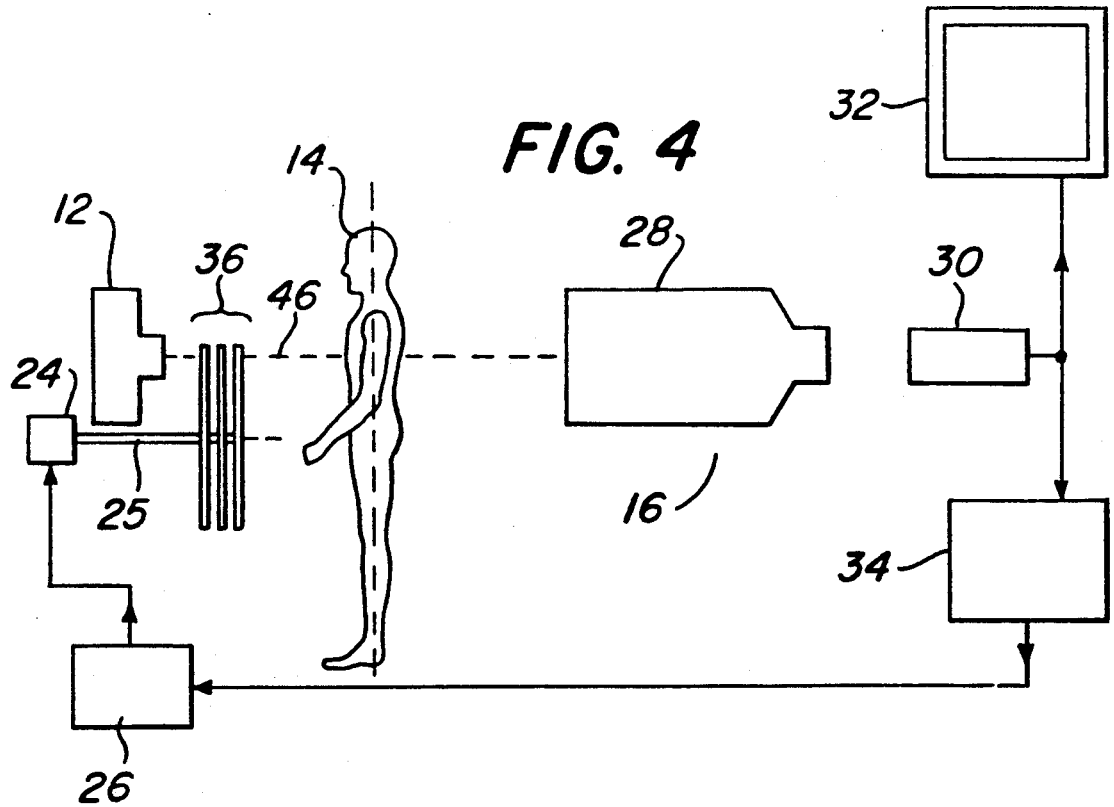

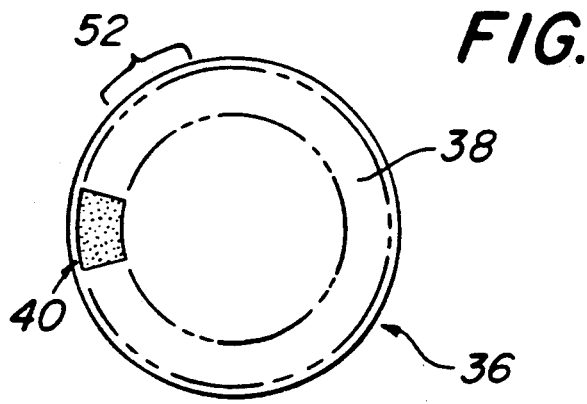
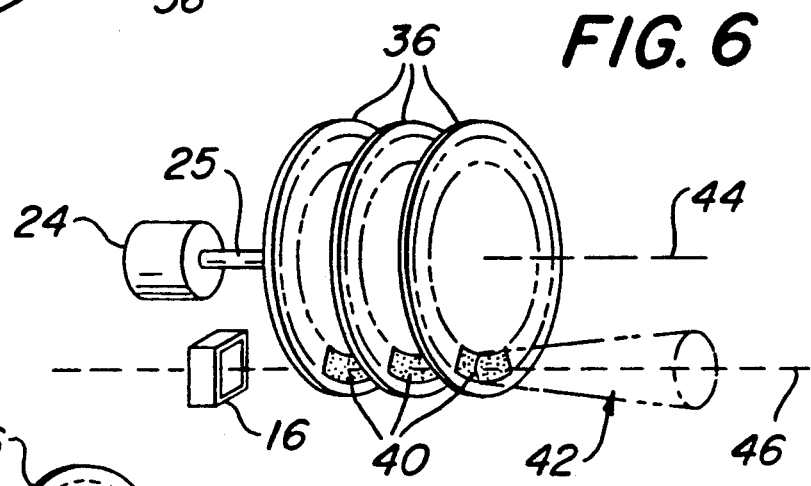
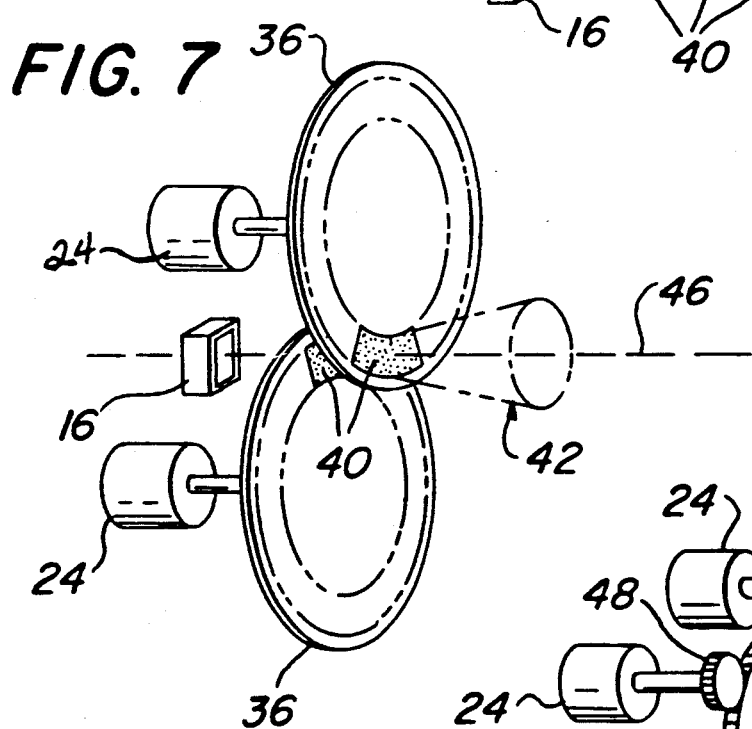
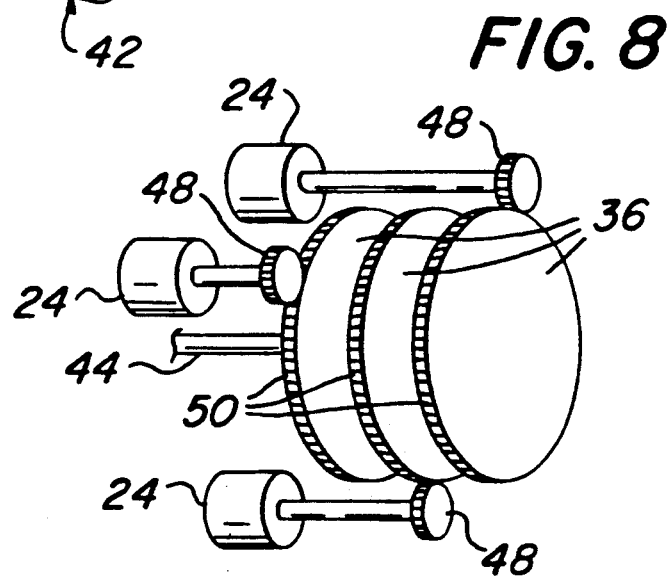

RADIOGRAPHIC EQUALIZATION APPARATUS AND METHOD

FIELD OF THE INVENTION

The present invention relates generally to the area of x-ray radiography. More particularly, the present invention relates to an equalization system for fluoroscopic and radiographic diagnostic x-ray systems.

BACKGROUND OF THE INVENTION

Equalization is a common term in the x-ray radiography field which refers to the process of selectively attenuating portions of the x-ray beam that are too intense for the density of a corresponding portion of the patient or object ("subject") exposed to the x-ray. Without equalization, the resulting x-ray image (appearing on either film or a monitor) may have inconsistent overall exposure, manifested as light and dark areas in the image, as a result of corresponding variations in density in the exposed portions of the subject. The effect of equalization is to reduce the intrinsically large dynamic range of the x-ray beam intensities in order to accommodate the dynamic range limitations of the x-ray detector system. The most common detector systems employed in diagnostic x-ray radiography are film and image intensifier-TV systems, both of which have severely limited dynamic range.

Equalization is also useful in digital subtraction angiography (DSA). DSA is a known imaging technique where digital radiographic images are obtained both before and after injection of an iodine based dye into the vasculature, and then the two images are subtracted. DSA employs an x-ray image intensifier (fluoroscope) that is optically coupled to a high quality television chain and to a video digitizer. Although the image intensifier has a relatively large dynamic range (i.e., the ratio of the highest allowable signal intensities to the lowest is large), the TV camera presents substantial dynamic range limitations and thus limits the dynamic range of the entire imaging system.

It is known to equalize an x-ray radiographic image by selectively attenuating only those areas of the image that are determined to have been overexposed. One such method involves arranging a plurality of filters between the x-ray emitter and the image receptor. The filters are selected and arranged so that only the areas of over-exposure are attenuated. Practice of this method provides acceptable results once the correct combination of filters has been found. However, a serious drawback of this method is that it is cumbersome since filter selection and juxtaposition is a manual process, and can require time consuming trial and error for the correct combination to be found.

It is therefore desirable to provide an apparatus and method for performing selective equalization of x-ray radiographic images that is automated and rapid, but yet is simple and relatively inexpensive to implement. The present invention achieves these goals.

SUMMARY OF THE INVENTION

According to one embodiment of the invention, a plurality of juxtaposed members, such as disks, is provided wherein each disk has an annulus defining a filter region for attenuating electromagnetic radiation such as x-rays. The attenuation provided by the annular filter region of each disk varies throughout at least selected angular portions of the annulus. At least a portion of the annular filter region of each disk overlaps a portion of the annular filter region of all other disks. The members may be embodied as strips or belts. In such case, the surface of the member defines the filter and varies throughout its length.

Motive means are operatively coupled to the disks for selectively and independently rotating each disk relative to the other disks and relative to an electromagnetic radiation emitter, such as an x-ray emitter. The emitter is disposed to emit radiation along a path intersected by the overlapping portions of the filter regions. Rotation of a disk thereby alters attenuation of the radiation along the path and received by the image receptor. A control means is operatively coupled to the motive means for controlling the operation of the motive means to alter the attenuation provided by the overlapping filters.

According to a preferred embodiment of the invention, the filter of each disk is comprised of a plurality of adjacent and unique preselected attenuation or filtration patterns. Thus, rotation of a disk results in a selected, unique combination of attenuation or filtration patterns along the path, wherein the attenuated radiation has a pattern that corresponds to the selected combination of attenuation patterns.

According to yet a further embodiment of the invention, the control means is operative to rotate the disks to a selected position for irradiating a subject to obtain a preliminary non-attenuated image. The control means is operatively coupled to the image receptor to receive and process the preliminary image. The control means determines locations and magnitudes of unsuitable exposures (i.e., overexposures) in the preliminary image and rotates the disks to select one of the unique combinations of attenuation patterns to compensate for the regions of unsuitable exposures.

According to yet a further embodiment of the invention, each disk has an area in the annular region that provides substantially constant attenuation to electromagnetic radiation and defines a parked position of the disk. The disks are rotatable to substantially align the parked positions with the path when it is desired to obtain the preliminary image.

BRIEF DESCRIPTION OF THE DRAWINGS

FIG. 1 illustrates a conventional, prior art x-ray system.

FIGS. 2 and 3 illustrate the overexposure problem inherent in the prior art system of FIG. 1.

FIG. 4 is a block diagram of a radiographic equalization apparatus according to the present invention.

FIG. 5 illustrates a disk provided in accordance with the practice of the present invention.

FIG. 6 illustrates one embodiment for an arrangement of the disks according to the invention.

FIG. 7 illustrates another embodiment for the arrangement of the disks according to the present invention.

FIG. 8 illustrates one embodiment of a means for selectively and independently rotating each of the disks according to the present invention.

DETAILED DESCRIPTION OF THE PREFERRED EMBODIMENTS

Figure 9:
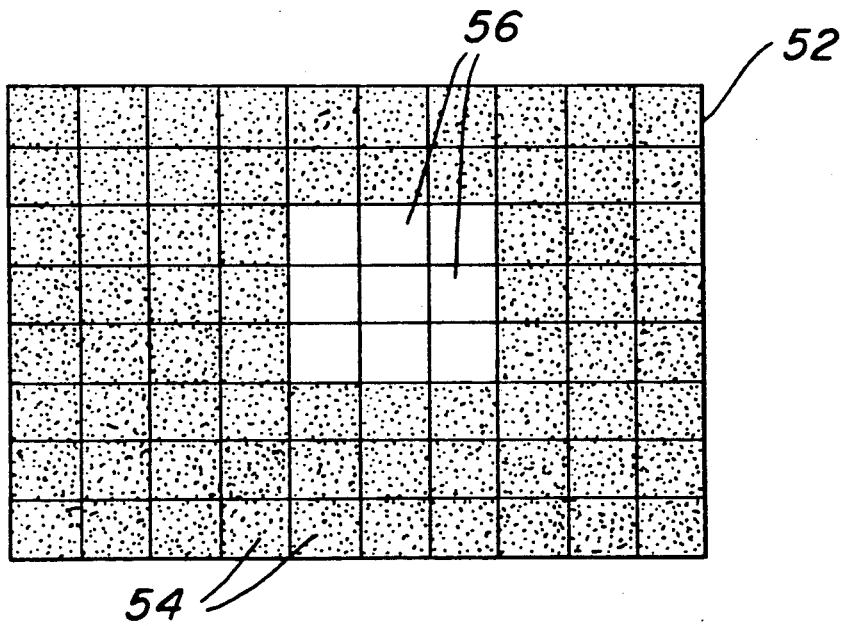
FIG. 9 illustrates a filtration pattern, or equalization window, resulting from practice of the present invention.

Referring now to the drawings, wherein like numerals represent like elements, there is illustrated in FIGS. 1, 2 and 3 a depiction of the problem in the prior art. As is conventional, a radiographic or fluoroscop x-ray system 10 comprises a radiographic emitter 12 for emitting radiation, typically x-rays. The emitted radiation travels along a path 46 wherein it impinges upon and passes through a portion of a subject 14, typically a portion of the anatomy of a person, or possibly, a portion of an object. The radiation strikes an image receptor 16, such as x-ray film or a fluoroscope, and exposes portions of the receptor 16 according to the amount by which various portions of the x-rays were attenuated while passing through corresponding portions of the subject 14.

FIG. 1 illustrates the typical scenario of a chest x-ray. Ideally, the x-rays would create an image 18 on image receptor 16 wherein all relevant details of lungs 20 and heart 22 are apparent from the x-ray image 18. The ideal scenario is illustrated in FIG. 2. However, since the x-rays impinging upon the subject 14 are of relatively constant intensity across the x-ray beam's diameter, but the densities of the two organs (lungs and hearts) through which the x-rays pass vary greatly, an image 18' such is illustrated in FIG. 3 more commonly results. Thus, as shown in FIG. 3, the image 18' of the lungs 20 (which are of relatively low density tissue) may be overexposed, while the image 18' of the heart 22 (which is a relatively high density muscle) may be correctly exposed or even underexposed. This can be a particular problem in digital subtraction angiography ("DSA") since, although the x-ray image intensifier typically associated with DSA systems has a relatively large dynamic range, the TV camera associated with DSA systems has dynamic range limitations and therefore limits the dynamic range of the entire imaging system.

FIG. 4 illustrates an embodiment of the present invention as implemented with a DSA system. As is conventional, a DSA system comprises a fluoroscope 28 for receiving x-rays and converting the received x-rays into visible light. The so converted visible light is shone into a high resolution television camera 30, so that image 18 can be realized on a monitor 32. The video data from the camera 30 is also provided to a video digitizer 34 which converts the analog video data into digital data, or a digital image, and provides it a processor 26. Typically, in DSA systems, the processor 26 is programmed to store digital radiographic images obtained both before and after injection of an iodine-based dye into vasculature and then subtract the two images to provide an image of the vasculature.

According to the invention, a plurality of stacked or juxtaposed members, such as disks or filter wheels, 36 are disposed so as to intersect the path 46 of radiation emitted by emitter 12, as shown. As will be described in more detail hereinafter, each disk 36 is independently rotatable by a motive means 24, such as a motor, mechanically coupled to each of the disks by one or more drive means 25. The motive means 24 operates under control of the processor (controls means) 26 in a manner to be described hereinafter. Each disk 36 is arranged so that the radiation emitted by emitter 12 passes through an annular region thereof that defines an annular filter region for attenuating the emitted radiation by an amount and/or pattern that is dependent upon the angular position of each disk 36.

Referring to FIG. 5, a single disk 36 is shown. The annular region 38 defines the filter region. As will become apparent hereinafter, the attenuation provided by the annular filter region varies throughout selected angular portions of the annular region 38. It will therefore be appreciated that when the plurality of disks 36 are arranged so that at least a portion of the filter region of each disk overlaps a portion of the filter region of all other disks (as shown in FIGS. 4, 6 and 7), then rotation of any disk 36 relative to the other disks will alter the total attenuation provided by the plural disks 36. According to a preferred embodiment of the invention, the filter region is comprised of a plurality of filter patterns 52, described in more detail hereinafter, angularly disposed around the annulus. Thus, rotation of any disk will, in this latter embodiment, result in a change in the attenuation pattern.

Preferably, each disk 36 has a region 40 of substantially homogeneous material that provides substantially zero or constant attenuation to radiation passing therethrough. By constant attenuation, it is meant that the region 40 of each disk provides the same amount of attenuation as the regions 40 of every other disk, i.e., either zero or the same amount of non zero attenuation. The region 40 therefore defines a constant attenuation region. The disk 36 is in a "parked" position when the region 40 is in substantial alignment with the path 46 of emitted radiation. According to a presently preferred embodiment of the invention, described in more detail hereinafter, all of the disks 36 are rotated to the parked position to obtain a preliminary or "prescan" image where the emitted radiation is not attenuated by the disks 36. The disks are shown in the parked position in FIGS. 6 and 7.

The disks may be arranged concentrically, as shown in FIG. 6 or in any other overlapping relationship, such as that shown in FIG. 7. The important consideration, however, is that the annular regions 38 of each disk that define the filter regions be arranged in a substantially overlapping and preferably parallel relationship. In the arrangement of FIG. 6, wherein the disks 36 are substantially concentric, each disk is rotated about a common axis 44 via the motive means 24 and drive means 25. Importantly, each of the individual disks 36 must be independently and selectively rotatable by the drive means 25. Any well known drive means 25, such as that illustrated in FIG. 8 and described below, may be employed for such purpose. As another example, the drive means 25 may comprise a plurality of independently operable clutches for selectively rotating a single disk relative to the other disks when the motive means 24 is actuated.

As shown in FIG. 6, the plural disks 36 are arranged so that their annular regions 38 defining the filter regions intersect the path 46 of the x-ray beam 42. Similarly, in the embodiment of FIG. 7 wherein the disks are not concentrically arranged, the overlapping portions of the annular regions 3 defining the filter regions intersect the path 46 of the x-ray beam 42 emitted by the emitter 12. As shown in FIG. 7, when the disks are not concentrically arranged, each disk 36 may be driven by a separate motive means 24, each under the control of the processor 26.

FIG. 8 illustrates an example of a drive means 25 that may be employed with the concentric disk embodiment of FIG. 6. As shown, a plurality of motive means 24 may be provided, each of which engages a different one of the disks 36. As before, each motive means 24 is operable under control of the processor 26. Each motive means 24 is mechanically coupled to a drive gear 48 which cooperates with teeth 50 circumferentially disposed around each disk 36. Thus, actuation of any one of the motive means 24 will result in rotation of an associated disk 36 without disturbing the angular position of the other disks 36.

Figure 11:
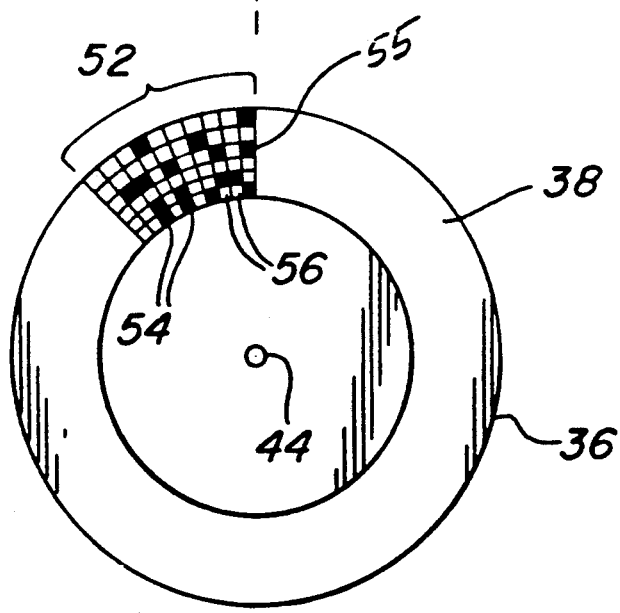

As mentioned, the filtration or attenuation provided by the annular region 38 varies with the angular positioning of the disks 36. Each disk may be of a simple construction wherein the amount of attenuation or filtration is constant across the radius of a selected portion of the annular region 38 but increases, either linearly or non-linearly, as the angular position around the annular region 38 is changed. For example, the filtration provided by the annular region 38 may be relatively low in a region adjacent to an upper peripheral edge of the zero attenuation region 40, but may increase as the annular region 38 is traversed in clockwise (or counterclockwise) fashion. However, according to a preferred embodiment of the invention, the annular region 38 is comprised of a plurality of unique filter patterns 52, such as shown in FIGS. 9 and 11. Each filter pattern 52 preferably comprises a plurality of discrete cells 55 arranged in a matrix, and each cell provides either attenuation (e.g., cells 54) or no attenuation (e.g., cells 56). The amount of attenuation provided by cells 54 may be complete (i.e., fully occlusive) or partial. The latter case allows for an arrangement wherein the magnitude of attenuation provided by the plural disks at any point in the image may be adjusted by overlapping a fewer or greater number of cells 54 of different disks 36. It will therefore be appreciated that, by proper selection of the filter patterns 52, the plural disks 36 may be rotated to provide an attenuation pattern that is both unique and selected to attenuate only those portions of the image 18 that are determined to have been overexposed. For example, proper selection of the filter patterns 52, combined with proper rotation of the plural disks 36, may result in a filtration pattern such as that shown in FIG. 9 well suited to solving the chest x-ray problem described in connection with FIGS. 2 and 3. It will be appreciated that the exemplary filtration pattern of FIG. 9 will allow less radiation to impinge upon the lung areas 20 than impinges upon the heart area 22, thereby creating an image that more closely approximates the ideal image 18.

The filter patterns 52 of each disk 36 that are aligned with the path 46 of emitted radiation collectively define a "filtration" or "equalization" window. Thus, the pattern of FIG. 9, which results from selective rotation of the disks 36, may be considered as one example of an equalization window.

Figure 10:
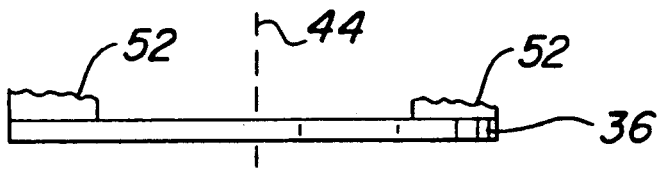
FIGS. 10 and 11 illustrate two different embodiments for implementing the attenuation or filtration patterns on the disks according to the present invention.

Each filter pattern 52 may be defined by a plurality of discrete irregularities in the surface of each disk 36 so as to define the various cells 55 therein as shown in FIG. 11. However, alternatively, the patterns 52 may be embodied as a substantial continuum or substantially continuous irregularity in the surface of each disk 36, as shown in FIG. 10. The continuum may be embodied as a surface of varying thickness. Thus, in the embodiment of FIG. 10, the surface thickness of each area of irregularity will determine the amount of attenuation provided thereby. The details of constructing the filter regions 52 will be described hereinafter.

Figure 12:
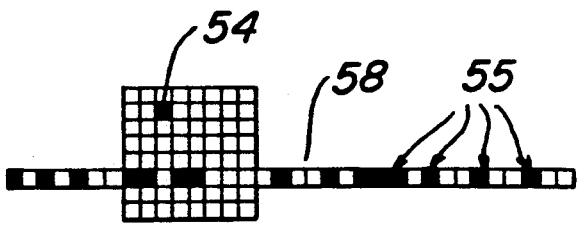
FIG. 12 illustrates a filtration pattern that consists of a single track according to a most presently preferred embodiment of the invention.

FIG. 12 illustrates how filtration or equalization windows are provided according to a most preferred embodiment of the invention. In the embodiment of FIG. 12, a single "filter track" 58 is provided in the annular region 38 of each disk. Each "filter track" 58 comprises a plurality of contiguous cells 55, and the cell pattern (i.e., the attenuation/no attenuation sequence) of each filter track is identical. The filter track 58 of each disk 36 is radially offset with respect to the filter track 58 of every other disk 36. Hence, by rotating the plural disks 36, a unique equalization window, comprising a matrix of cells 55, can be obtained. Thus, by selective rotation of the disks 36, a selected combination of attenuation patterns can be obtained whereby the attenuated radiation has a pattern that corresponds to the selected combination of attenuation patterns. The control means 26 is operative to actuate the motive means 24 so as to automatically select the combination of attenuation patterns and thereby alter the attenuation provided by the overlapping filters.

The cells 55 may be formed by a stamping or milling process to form depressions and peaks (i.e., areas of greater and lesser thickness) in the attenuation material so as to provide areas of attenuation and no attenuation. Practical considerations that should be taken into account are set forth below. In the embodiment of FIG. 10, wherein the filter region is a substantial continuum, a milling process is preferred. The thickness of the depressions and peaks may vary to alter the amount of attenuation provided. In either case, the filter patterns may be constructed from images that define the designed patterns. Images of each disk, as a function of disk angle, may be made using a low resolution x-ray camera, and then inverted (e.g., black to white and white to black). The inverted image of the disk at a given angle is the image which would be perfectly equalized by the disk at that angle.

In a preferred embodiment, the processor 26 is operative to rotate the disks to the parked position for irradiating the subject 14 to obtain a preliminary radiographic image. The processor 26 may be programmed to process the preliminary image, according to well-known techniques, and determine the locations and magnitudes of unsuitable exposures (i.e., those of overexposure) in the preliminary image. The control means thereafter rotates the disks 36 to select one of the unique combination of attenuation patterns to compensate for the overexposures.

In the foregoing description of the preferred embodiment, the members have been described as disks. However, the invention is not limited to the use of disks for the members. As one alternative, for example, the members may be strips or belts wherein the surface of each strip or belt defines the filter region, and the amount of attenuation varies throughout the length of the strip or belt. In such case, the motive means would move or index each of the strips or belts in a longitudinal direction to achieve the selective attenuation described above. Implementation of a system that imploys strips or belts, instead of the described system using disks, will be readily apparent to those skilled in the art.

A number of practical considerations that should be kept in mind in the practice of the present invention will now be discussed.

There are practical limitations as to how many disks 36 can be physically located next to the emitter 12. The number of disks selected is a trade off between what is practical from physical and economic considerations, and the degree of flexibility required for the specific application. A large number of disks will allow for more flexibility, but will also result in more bulk, complexity and expense. In one exemplary embodiment, four 14" disks 36 are provided. At a source to image distance of 100 cm, and with disks 36 placed 10 cm from the focal point, and further, for a 14" diameter image intensifier input phosphor and a 16 cell × 16 cell equalization window, the size of each cell 55 on each disk 36 would be 2.2 mm. This would allow for 379 discrete positions around the 14" disk. With four disks, the number of equalization patterns is $379^4 = 2 \times 10^{10}$.

The spacial distribution of attenuating material on each disk is also an important consideration. For ease of explanation, assume an 8 cell x 8 cell equalization window and eight 10" disks in the system. If the embodiment of FIG. 12 is employed, each disk 36 is responsible for its own linear segment over the 8 cell × 8 cell surface. With a magnification factor of 10, approximately 252 cells can be positioned around a 10" disk (assuming a 23 cm diameter image intensifier). The 8 cells within a window at any given degree of rotation are contiguous on the disk, and, for binary equalization (i.e., each cell provides either attenuation or no attenuation), there are $2^8 = 256$ different equalization window patterns possible. Though there are approximately 256 different positions around the annulus for this one 8-cell track, there are only 32 unique positions around the annulus (i.e., 256/8). Thus, a contiguous 256 element pattern of filtration that produces the 256 possible equalization patterns must be developed. The development may be performed on a computer by employing iterative techniques. For example, beginning with 7 blank cells, the next cell's value (0=no filtration, 1=filtration) is randomly chosen at 0 or 1, and the computer may check the resulting 8-element pattern (the present cell plus the last 7 to see if it already exists). If it is redundant, the cell is toggled (1 to 0 or 0 to 1), and then the next cell value chosen randomly, and so on. After 249 iterations, the number of unique versus redundant patterns will be determined. All disks 36 should have the same pattern, although their radial displacement will be different.

The composition of the material from which the disk and attenuator are constructed must also be taken into consideration. The filters should be composed of a material that will attenuate the desired amount of x-ray radiation without being too thick. Moreover, to accommodate several filters, the disks 36 must be able to be packed into a relatively thin array that can be placed between the x-ray tube and the x-ray collimator. If the attenuation material is too efficient, then the small thicknesses will present machine tolerance problems, i.e., a small machining error would result in too much or too little filtration. The half value layers of copper at 30 and 40 keV (the approximate range of effective energies common in DSA) are 0.072 mm and 0.16 mm, respectively, and the tenth value layers (the thickness necessary to reduce the beam intensity to 10%) are 0.24 mm and 0.54 mm, respectively. These thicknesses meet the above thickness criteria, and thus copper is well suited to this application. Other materials may be practical at production level quantities and may be silk screened or photo-etched onto the disks 36. The disks themselves should be manufactured of a strong, thin, relatively radiolucent material onto which the copper filtration material can be affixed, such as DELRIN ®.

The diameter of each disk 36 in the system is a compromise between bulk and flexibility. Larger diameter disks 36 have greater circumferential areas for the annular regions 38, and consequently more patterns 52 may be placed on each disk 36. It has been determined from measurement of several x-ray systems commonly employed in angiography that disks ranging between 8" and 14" diameters are feasible.

The magnification of the image provided by each disk 36 is determined by the disk's relative position between the x-ray focal spot and the image receptor. By positioning the disks 36 as close as possible to the x-ray source 12, smaller filtration patterns 52 are required on the disks 36. This means that, for a given diameter of disk, more equalization patterns can be accommodated. Additionally, the greater the magnification, the more blurred the image of the filtration pattern will be. For example, for a magnification factor of 10, the blur zone (penumbra) would extend several centimeters at the image plane for a 2.3 mm square copper filter. The degree of blurring (due to the finite size of the focal spot) dictates the effective bandwidth of frequencies that can be equalized, and greater magnification implies lower frequency equalization. This is desirable, since the purpose of equalization is to filter low frequency components out of the x-ray beam striking the image receptor 16. For a complete discussion of bandwidth considerations for chest radiography, see Hasegawa, S. N. et al., "Digital Beam Attenuator Technique For Compensated Chest Radiography", *Radiology*, No. 172, pp. 537–543 (1986). If the invention is employed in connection with DSA, then the disks should be placed as close as possible to the x-ray source 12 to minimize the size of the filtration patterns 52 and maximize the number of possible patterns.

Use of neural networks has been determined to provide an efficient method for determining the best angle of rotation for each disk, given the preliminary or pre-scan image. Once the number of disks 36 and filter surfaces have been determined, images of the disks 36 can be acquired using either simulation or experimental acquisition, as above described. Since the rotation angles are known along with the filtration patterns 52, a neural network may be trained to generate disk rotation angles, given the images to be equalized. See Rumelhart, D. E. et al., *Parallel Distributed Processing*, MIT Press, Vol. 1, Cambridge, Mass. (1986). See also Boone, J. M. et al., "Neural Networks in Radiology: An Introduction and Evaluation in a Signal Detection Task", *Medical Physics*, Vol. 17, no. 2 (1990); Boone, J. M. et al., "Computer Aided Radiologic Diagnosis Using Neural Networks", *Proceedings of the International Joint Commission on Neural Networks*, January, 1990; Boone, J. M., "Neural Network Scatter Correction Technique For Digital Radiography", SPIE, No. 1231, (1990); Gross, G. W., et al. "Application of Neural Networks to Neonatal Chest Radiographic Diagnosis", *Radiology*, No. 173 (supplement), p. 464 (1989); Boone, J. M. "Neural Networks in Radiologic Diagnosis: An Introduction and Illustration", *Invest. Radiology*, (1990); and, Gross, G. W., "Neural Networks in Radiologic Diagnosis: Neonatal Chest Radiography", *Invest. Radiology*, (1990). All of the foregoing references are incorporated herein by reference.

In the design of the surface irregularities of each disk, Fourier analysis is helpful. Equalization is a low frequency effect; that is, the images of the disks will appear very fuzzy or blurry, and not crisp or distinct. The frequencies necessary for equalization are on the order of one to ten hertz per image. For a chest radiograph, for example, this would correspond to a maximum frequency of 0.03 line pairs per millimeter. This frequency is about 100 times lower than the highest frequency components in chest radiographs (about 3 line pairs per mm). The simplest solution for the surface relief of the disks is to have each disk correspond to one or two frequencies at a few different orientations to the cartesian image frame. The angulation of the disk is the phase angle, and the superposition of several disks of different frequencies corresponds to a Fourier series with only a few terms. When implemented in this fashion, a test exposure is made, the test exposure image analyzed and the disks positioned for the acquisition image in a few seconds.

There has been described an efficient and effective radiographic equalization apparatus. The present invention may be embodied in other specific forms without departing from the spirit or essential attributes thereof and, accordingly, reference should be made to the appended claims, rather than to the foregoing specification, as indicating the scope of the invention.

What is claimed is:

1. Apparatus comprising:
   (a) a plurality of juxtaposed members, each member having a surface defining a filter for attenuating electromagnetic radiation, the filter of each member being comprised of a plurality of adjacent and unique preselected attenuation patterns, the attenuation provided by the filter varying throughout at least selected portions of the surface, at least a portion of the filter of each member overlapping a portion of the filter of all other members;
   (b) motive means operatively coupled to the members for independently moving each member relative to an electromagnetic radiation emitter, the emitter being disposed to emit radiation along a path intersected by the overlapping portions of the filters, movement of a member altering attenuation of the radiation along the path; and,
   (c) control means operatively coupled to the motive means for controlling the operation of the motive means to alter attenuation provided by the overlapping portions of the filters.

2. Apparatus according to claim 1 wherein each member is a disk, the surface is an annulus of the disk and the movement provided by the motive means is rotation of a disk.

3. Apparatus according to claim 2 wherein each disk has an area in the annulus that provides substantially constant attenuation to electromagnetic radiation and defining a constant attenuation region, and the disks are rotatable to substantially align the constant attenuation regions of each disk with the path to define a parked position.

4. Apparatus according to claim 3 wherein the control means is operative to rotate the disks to the parked position for irradiating a subject to obtain a preliminary radiographic image.

5. Apparatus according to claim 4 wherein the control means is operative, based upon the preliminary image, to rotate the disks and thereby alter the attenuation provided by the overlapping filters to adjust for at least overexposures in the preliminary image.

6. Apparatus according to claim 2 wherein the electromagnetic radiation comprises x-rays.

7. Apparatus according to claim 6 wherein rotation of a disk results in a selected, unique combination of attenuation patterns along the path, the attenuated radiation having a pattern that corresponds to the selected combination of attenuation patterns.

8. Apparatus according to claim 7 wherein the control means is operative to rotate the disks to a selected position for irradiating a subject to obtain a preliminary radiographic image and being operatively coupled to receive and process the preliminary image, the control means further comprising means for determining locations and magnitudes of at least overexposures in the preliminary image, the control means rotating the disks to select one of the unique combinations of attenuation patterns to compensate for the regions of overexposure.

9. Apparatus according to claim 8 wherein each disk has an area in the annulus that provides substantially constant attenuation to electromagnetic radiation and defining a constant attenuation region, and the disks are rotatable to substantially align the constant attenuation regions of each disk with the path to define said selected position.

10. Apparatus according to claim 1 wherein each pattern is defined by a plurality of discrete cells in a surface of the disk.

11. Apparatus according to claim 1 wherein each pattern is defined by a substantially continuum of irregularities in a surface of the disk.

12. Apparatus according to claim 10 or 11 wherein the patterns are formed by variations in a thickness of the filter.

13. Apparatus according to claim 2 wherein the disks are substantially concentric.

14. Apparatus according to claim 2 wherein the disks are non-concentric but are disposed in substantially parallel planes.

15. Apparatus comprising:
   a) a plurality of juxtaposed disks, each having an annular filter region for attenuating electromagnetic radiation according to preselected patterns defining attenuation patterns, the attenuation patterns varying throughout at least selected angular positions along the filter region of each disk, at least a portion of the filter region of each disk overlapping a portion of the filter region of all other disks;
   b) motive means operatively coupled to the disks for independently rotating each disk relative to an electromagnetic radiation emitter disposed to emit radiation along a path that is intersected by the overlapping portions of the filter regions, rotation of a disk relative to the emitter attenuating emitted radiation according to a selected combination of attenuation patterns, the attenuated radiation having a pattern defining a radiation pattern that corresponds to the selected combination of attenuation patterns; and
   c) control means operatively coupled to the motive means for automatically selecting the combinations of attenuation patterns to alter attenuation provided by the overlapping portions of the filter regions.

16. Apparatus according to claim 15 wherein each disk has an annular area that defines a constant attenuation region for providing substantially constant attenuation to electromagnetic radiation, and the disks are rotatable to substantially align the constant attenuation regions of each disk with the path to define a parked position, the control means being operative to rotate the disks to the parked position for irradiating a subject to obtain a preliminary radiographic image.

17. Apparatus according to claim 16 wherein the control means is operatively coupled to receive and process the preliminary image, and the control means further comprises means for determining locations and magnitudes of at least overexposures in the preliminary image, the control means rotating the disks to select one of the unique combinations of attenuation patterns to compensate for the overexposures.

18. Apparatus according to claim 16 wherein the filter of each disk is comprised of plurality of adjacent and unique preselected attenuation patterns.

19. Apparatus according to claim 19 wherein each pattern is defined by a plurality of discrete cells in a surface of the disk.

20. Apparatus according to claim 18 wherein each pattern is defined by a substantial continuum of irregularities in a surface of the disk.

21. Apparatus according to claim 19 or 20 wherein the patterns are formed by variations in thickness of the filter.

22. Apparatus comprising:
a) a plurality of juxtaposed disks, each having an annular filter region for attenuating x-rays according to preselected patterns defining attenuation patterns, the attenuation patterns varying throughout at least selected angular positions along the filter region of each disk, the attenuation patterns being defined by one of a plurality of discrete cells or a substantial continuum of irregularities in a surface of each disk, at least a portion of the annular region of each disk defining a constant attenuation region for providing substantially constant attenuation to x-ray, at least a portion of the filter region of each disk overlapping a portion of the filter region of all other disks;
b) motive means operatively coupled to the disks for independently rotating each disk relative to an x-ray emitter, the emitter being disposed to emit x-ray along a path intersected by the overlapping portions of the filter regions, rotation of a disk relative to the emitter attenuating emitted radiation according to a selected combination of attenuation patterns, the attenuated radiation having a pattern defining a radiation pattern that corresponds to the selected combination of attenuation patterns, the motive means being operative to substantially align the constant attenuation region of each disk with the path to define a parked position for irradiating a subject to obtain a preliminary radiographic image; and,
c) control means operatively coupled to the motive means for automatically selecting the combinations of attenuation patterns to alter attenuation provided by the overlapping portions of the filter regions, the control means being operatively coupled to receive and process the preliminary image, the control means further comprising means for determining locations and magnitudes of at least overexposures in the preliminary image, the control means rotating the disks to select one of the unique combinations of attenuation patterns to compensate for the overexposures.

23. Apparatus according to claim 22 wherein the patterns are formed by variations in thickness of the filter.

24. Method comprising:
a) providing a plurality of juxtaposed disks, each having an annular filter region for attenuating electromagnetic radiation according to preselected patterns defining attenuation patterns;
b) rotating the disks to a preselected angular position;
c) irradiating a subject with electromagnetic radiation directed through the annular regions of each disk when the disks have been rotated to the preselected angular position to obtain a preliminary image;
d) determining locations and magnitudes of at least overexposures in the preliminary image; and,
e) rotating, based upon step (d), at least one disk to select a unique combination of attenuation patterns and irradiating the subject with electromagnetic radiation directed through the selected patterns, the attenuated radiation having a pattern corresponding to the selected combination of attenuation patterns, the combination of attenuation patterns being selected to compensate for the overexposures in the preliminary image.

25. Article comprising a disk having an annulus at least a portion of which defines a filter for attenuating electromagnetic radiation according to preselected radiation patterns, the patterns varying throughout angular positions along the annulus, the attenuation patterns being defined by one of a plurality of discrete cells or a substantial continuum of irregularities in a surface of the disk.

26. Article according to claim 25 wherein a portion of the annulus of the disk contains a region defining a constant attenuation region for providing substantially constant attenuation to electromagnetic radiation.

27. Article according to claim 25 wherein the patterns are defined by variations in a thickness of the filter.

28. Article according to claim 27 wherein the variations in the thickness of the filter are defined by stamped depressions and peaks of varying thickness in the annulus.

29. Article according to claim 27 wherein the variations in the thickness of the filter are defined by milled depressions and peaks of varying thickness of the annulus.

* * * * *